US007955276B2

(12) United States Patent
Yoshino

(10) Patent No.: US 7,955,276 B2
(45) Date of Patent: Jun. 7, 2011

(54) CAPSULE ENDOSCOPE

(75) Inventor: Koichiro Yoshino, Tokyo (JP)

(73) Assignee: Olympus Corporation, Tokyo (JP)

( * ) Notice: Subject to any disclaimer, the term of this patent is extended or adjusted under 35 U.S.C. 154(b) by 399 days.

(21) Appl. No.: 12/334,410

(22) Filed: Dec. 12, 2008

(65) Prior Publication Data

US 2009/0099416 A1 Apr. 16, 2009

Related U.S. Application Data

(63) Continuation of application No. 10/933,314, filed on Sep. 3, 2004, now Pat. No. 7,505,802.

(30) Foreign Application Priority Data

Sep. 5, 2003 (JP) ................................ 2003-314708

(51) Int. Cl.
*A61B 5/103* (2006.01)

(52) U.S. Cl. .......... 600/587; 600/407; 600/476; 348/68; 348/76; 348/77

(58) Field of Classification Search .................. 600/172, 600/302, 476, 547, 153, 114, 424, 350, 593, 600/582, 477, 109, 473, 160, 101; 348/68, 348/76, 77, 301, 370
See application file for complete search history.

(56) References Cited

U.S. PATENT DOCUMENTS

| | | | | |
|---|---|---|---|---|
| 4,638,353 | A * | 1/1987 | Nagasaki et al. | 348/70 |
| 5,313,306 | A * | 5/1994 | Kuban et al. | 348/65 |
| 5,602,676 | A * | 2/1997 | Estelle | 359/557 |
| 6,108,005 | A * | 8/2000 | Starks et al. | 345/419 |
| 7,215,477 | B2 * | 5/2007 | Yamasaki et al. | 359/649 |
| 2003/0158503 | A1 * | 8/2003 | Matsumoto | 600/593 |

* cited by examiner

*Primary Examiner* — Brian Casler
*Assistant Examiner* — Nasir Shahrestani
(74) *Attorney, Agent, or Firm* — Arnold International; Bruce Y. Arnold

(57) ABSTRACT

A capsule endoscope is disclosed that includes a capsule and a transparent cover having a central axis and that is located in front of an objective optical system within the capsule. The objective optical system has a depth of field, a field of view, and an image surface that has curvature of field, and is arranged on the central axis of the transparent cover and the capsule. The field of view of the objective optical system includes a spherical surface that is tangent to the transparent cover at a periphery of the field of view, and the near point of the depth of field on the optical axis of the objective optical system is positioned farther from the objective optical system than is the transparent cover. Various conditions are satisfied so as to provide high quality imaging.

2 Claims, 13 Drawing Sheets

OBJECT PLANE THAT IS ASSUMED UPON ACTUAL USE

HYPOTHETICAL SPHERICAL SURFACE

DEPTH OF FIELD THAT IS REQUIRED IN THE CENTER OF THE FIELD OF VIEW

RANGE OF THE DEPTH OF FIELD

INTERMEDIATE ANGLE OF VIEW

MAXIMUM ANGLE OF VIEW

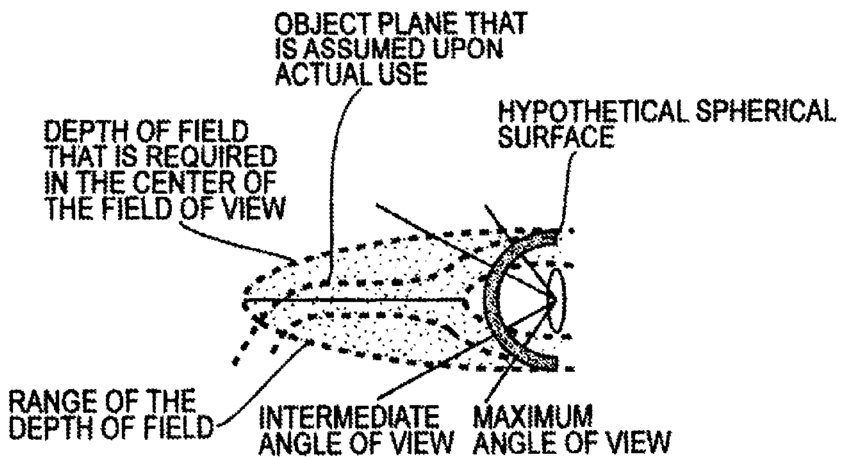
FIG. 6(a)
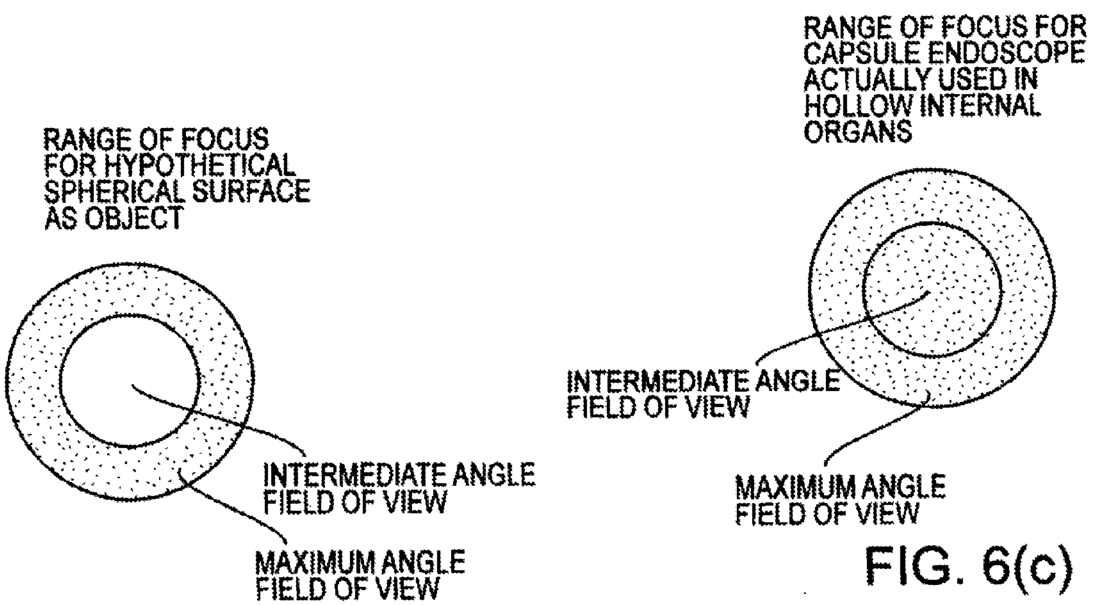
FIG. 6(c)
FIG. 6(b)

CAPSULE ENDOSCOPE

This is a Continuation Application of copending U.S. application Ser. No. 10/933,314 filed Sep. 3, 2004, and claims the benefit of priority of Japanese Patent Application 2003-314708 filed Sep. 5, 2003, the disclosure of which is hereby incorporated by reference.

BACKGROUND OF THE INVENTION

In recent years, endoscopes have been widely used in both the medical and industrial fields. Recently, a capsule endoscope has been introduced for use in medical applications that can be swallowed by a patient; see for example, FIG. 1 of Japanese Laid-Open Patent Application 2001-91860 and FIG. 1 of International Patent Publication WO 01/65995 A2. Such endoscopes are advantageous in that they greatly reduce the pain associated with an endoscopic examination by avoiding the pain associated with inserting the insertion portion of a conventional endoscope.

Japanese Laid-Open Patent Application 2001-91860 discloses a conventional capsule endoscope wherein an objective lens and an illumination made from light emitting diodes that are symmetrically positioned about the objective lens, are provided inside a roughly hemispherical, transparent cover. A region of an objet that is illuminated by the light emitting diodes is imaged by the objective lens onto an image sensor. The capsule endoscope disclosed in International Patent Publication WO 01/65995 A2 has substantially the same construction as that shown in FIG. 1 of Japanese laid-Open Patent Application 2001-91860.

In these conventional examples, an objective tens is arranged along a central axis of a roughly-hemispherical, transparent cover that forms part of a capsule. However, when the radius of curvature of the transparent cover in a central portion of the field of view is the same as the radius of curvature near the periphery of the field of view, due to the fact that the radius of curvature of the transparent cover is determined according to the external diameter of the capsule, there is a problem in that the length of the capsule endoscope becomes excessive.

Further, in the above patent publications, nothing is mentioned at all concerning the conditions needed for providing an optimum observation field of view of a capsule endoscope.

BRIEF SUMMARY OF THE INVENTION

The present invention relates to a capsule endoscope that may be swallowed by a patient for the purpose of examining inside portions of a living body. More particularly, the present invention discloses various conditions to be met by a capsule endoscope in order to improve the ease with which the capsule may be swallowed by miniaturization of the capsule size while assuring an optimum depth of field and favorable correction of astigmatism over the entire field of view of the capsule endoscope.

BRIEF DESCRIPTION OF THE DRAWINGS

The present invention will become more fully understood from the detailed description given below and the accompanying drawings, which are given by way of illustration only and thus are not limitative of the present invention, wherein:

FIGS. 6(*a*)-6(*c*) are illustrations that show the depth of field of the objective optical system where the depth of field varies depending upon an angle of view;

FIG. 8(*b*) is a diagram that shows the relationship of the sagittal image surface S and the tangential image surface T relative to the image receiving surface of an mage pickup device when a hypothetical spherical surface near the periphery of the field of view is regarded as the object after focusing has been performed;

DETAILED DESCRIPTION

Figure 1B:
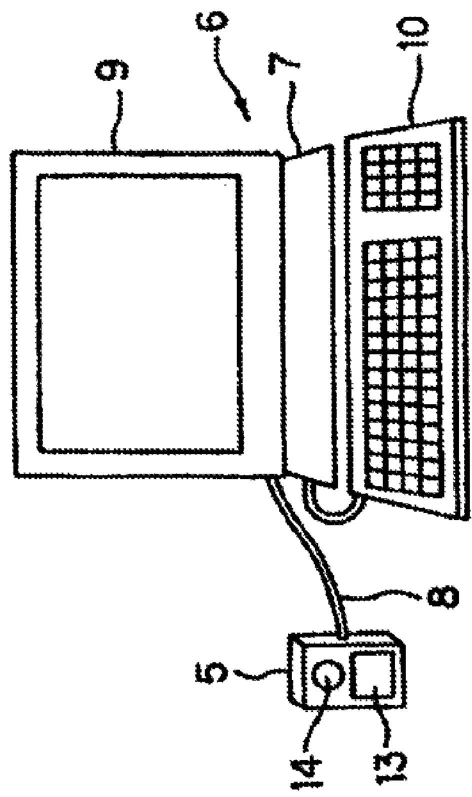
FIGS. 1(*a*) and 1(*b*) illustrate the various components that may be used when employing a capsule endoscope according to the present invention to examine internal regions of a living patient, with FIG. 1(*a*) showing components of a capsule endoscope system that may be either swallowed or worn by the patient, and FIG. 1(*b*) showing additional components that may be used to perform the examination.

The present invention relates to a capsule endoscope that includes: a capsule body having a central axis; an illuminator that illuminates the inside of a living body; an objective optical system having an optical axis that is aligned with the central axis of the capsule body and that forms an image of a region that is illuminated by the illuminator; an image detector for capturing images formed by the objective optical system; an adjustment device that enables the positions of the objective optical system and the image detector to be adjusted; and a transparent cover having a central axis that is aligned with the optical axis of the objective optical system. The transparent cover is positioned in front of the objective optical system and is formed such that the radius of curvature of a portion where a light ray at the periphery of the field of view of the objective optical system passes through is smaller than the radius of curvature of a portion where a light ray from the center of the field of view of the objective optical system passes through. Therefore, the present invention enables die reduction of the capsule size while retaining an adequate field of view for observation.

Further, the present invention provides the optimum depth of field for the capsule endoscope due to the following Conditions (1) and (2) being satisfied by the transparent cover.

$$2f^2\cdot(1-\cos(\theta max/2))/(D\cdot\cos(\theta max/2))+\Delta I\leqq 0 \qquad \text{Condition (1)}$$

$$0.4<IH\max/f \quad \text{Condition (2)}$$

where f is the composite focal length of the objective optical system;

θmax/2 is the angle of view at the maximum image height, as measured between the optical axis of the objective optical system and a chief ray;

D is the external diameter of the capsule endoscope;

ΔI is the amount of curvature of field when a flat object, at a distance D/2 from the object side of the objective optical system is observed, where ΔI is determined by averaging the amount of curvature of field of the tangential and sagittal image surfaces at the maximum image height as measured from the paraxial image plane; and IHmax is the maximum image height on the paraxial image plane.

In addition, it is preferable that the following Conditions (3) and (4) are satisfied within the range of viewing angles (as measured from the optical axis) from θ/2=40° through θmax/2:

$$a_o>0 \quad \text{Condition (3)}$$

$$a_p\leqq 0 \quad \text{Condition (4)}$$

where $a_o$ is the distance from a hypothetical spherical surface of radius of curvature R equal to D/2 to a near point of the depth of field, on the axis, and the direction away from the objective optical system is regarded as positive; and, $a_p$ is the distance from a hypothetical spherical surface of radius of curvature R equal to D/2 to a near point of the depth of field, off the axis, and the direction away from the objective optical system is regarded as positive.

It is further preferable that the following Condition (5) be satisfied:

$$2f^2\cdot(1-\cos(\theta\max/2))/IH\max^2\cdot\cos(\theta\max/2)\leqq P\cdot D \quad \text{Condition (5)}$$

where

P is the Petzval sum that is expressed using the following Equation (A)

$$P=\sum_{i=1}^{k}(1/n_{i-1}-1/n_i)(1/r_i) \quad \text{Equation (A)}$$

$n_i$ is the index of refraction of the given surface # i, in order from the object side, as indicated by the subscript, $r_i$ is the radius of curvature of the given surface # i, in order from the object side, as indicated by the subscript, and k is the number of surfaces.

Several embodiments of the present invention will now be explained in detail, with reference to the drawings.

Embodiment 1

Figure 1A:
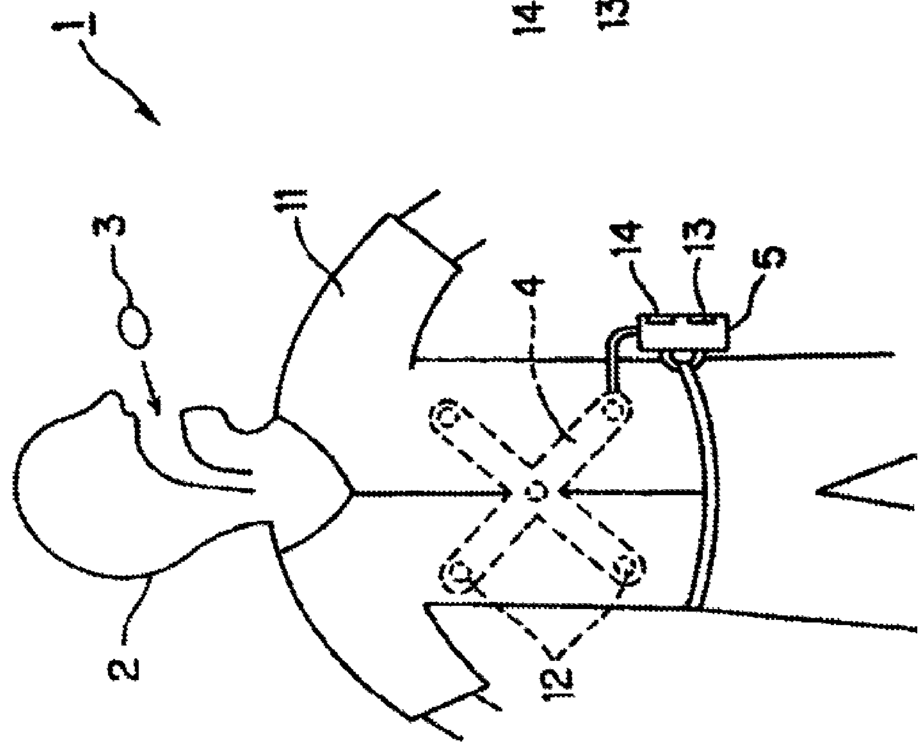

FIGS. 1(*a*), 1(*b*) and 2 relate to Embodiment 1 of the present invention. As shown in FIG. 1(*a*), a capsule endoscope device 1 is provided with a capsule endoscope 3 and an external unit 5. A patient 2 swallows the capsule endoscope 3 and, when the capsule endoscope 3 passes through a body passage within the patient's body cavity, an internal wall surface of the body passage is optically imaged and image data signals are transmitted from the capsule endoscope 3 via radio waves. The transmitted image data signals are received by an antenna unit 4 that is provided outside the body of the patient 2, and the image data signals are stored in an external unit 5. The external unit 5 has built-in memory, for example, a COMPACT FLASH MEMORY® having a storage capacity of 1 GB, for the purpose of storing the image data signals.

During the examination or after the examination, as shown in FIG. 1(*b*), the external unit 5 may be connected to a display system 6, so that the stored image data can be displayed.

The external unit 5 and the display system 6 which comprises a personal computer 7 (hereinafter referred to as PC 7) may be detachably connected to each other via a communication cable 8, such as a USB cable, in order to establish a communication link.

The image data stored in the external unit 5 may then be sent to the PC 7, and the data can be stored in the hard disk inside the PC 7 or displayed on a display section 9 after processing for the purpose of displaying the image data. A device for performing a data input operation, such as a keyboard 10, may be connected to the PC 7.

For the USB cable 8, any of the communication standards, USB 1.0, USB 1.1 or USB 2, are applicable. Other than these, a cable for performing serial data communication using the standard of RS-232C or IEEE 1394 is also applicable. However, the cable used is not limited to a cable for performing serial data communication, as a cable for performing parallel data communication may also be used.

As shown in FIG. 1(*a*), when an examination by an endoscope is performed by swallowing the capsule endoscope 3, the antenna unit 4 having multiple antennas 12 is attached inside an electromagnetic shielding shirt 11 that is worn by the patient 2 so as to shield the antennae unit 4 from noise sources such as other radio waves. The extend unit 5, for example, may be detachably attached to a belt worn by the patient 2 using a hook.

The external unit 5 may be, for example, a box shape, having on its front surface, for example, a liquid crystal monitor 13 that functions as a display unit where the image data is displayed, and an operation button 14 where the control operation is performed.

Further, the external unit 5 may be equipped with a two-way communication circuits a control circuit, a display circuit and an internal power source.

As shown in FIG. 25 in the capsule endoscope 3, the engagement of a transparent front cover 16 having a substantially hemispherical shape seals with a rear portion 17 of a capsule having an occluded rear section. The occluded rear section also has a substantially hemispherical shape amid thus the combination of the transparent front cover 16 and the rear portion 17 results in the formation of a capsule container having a watertight, sealed structure inside, and with an objective optical system 18 that is positioned inside the transparent front cover 16.

The objective optical system 18 may, be formed by attaching a first lens and a second lens to a first lens frame 20 and a second lens frame 21, respectively, that are arranged along the cylinder axis inside the front cover 16. A CMOS image detector 23 may be attached to the front surface of a substrate 22 and arranged at the image surface of the objective optical system 18. Further, one (or more) white LED(s) 25 may be attached to a substrate 24 that is secured so as to be engaged with the outer surface of the second lens frame 21. The substrate 22 where the CMOS image detector 23 is attached is electrically connected with a substrate which forms a drive processing circuit 27, and where electric parts are mounted via a connection section 26.

A substrate that includes a memory circuit 28 for storing image data is connected to the rear surface of the substrate that forms the drive processing circuit 27, via a connection section 29. A substrate that includes a radio wave communication circuit 30 is connected to the rear surface of the substrate that includes the memory circuit 28, via a connection section 31. In addition, two button-shaped batteries 32, 32 are arranged on the rear surface of the substrate that includes the radio wave communication circuit 30.

Also, an antenna 33 that is connected to the radio wave communication circuit 30 is arranged on the inside of the capsule next to the substrate that forms the drive processing circuit 27. Further, the anode of the bank of batteries 32, 32 is connected to a ground, such as the radio wave communication circuit 30, and the positive side of the power source of the radio wave communication circuit 30 is connected to one end of the lead section of a spring-state contact point member 35.

The spring-state contact point member 35 becomes a contact point section 36*a* on the rear surface of the bank of batteries 32, 32 and another contact point section 36*b* that is connected to the cathode of the battery 32 is arranged so as to be situated adjacent to the contact point section 36*a*. Normally, the OFF status is set by interposing an insulation string member 37 between the contact point sections 36*a* and 36*b*.

A portion of the insulation string member 37 is exposed to the outside via a small notch in a valve section 38 (or a rubber stopper section) established in the rear portion 17 of the capsule, and pulling out the insulation string member 37 results in setting the ON state by making contact between the contact point sections 36*a* and 36*b*. This action closes the valve section 38, and a watertight seal is maintained.

In the front cover 16, the inside and outside surfaces of the dome-shaped portion have constant radii of curvature Ri and Ro, respectively, from the center of the field of view up to the vicinity of the periphery of the field of view. In the present embodiment, Ri=6.0 mm and Ro=6.5 mm.

The centers of curvature of Ri and Ro coincide with the center of an entrance pupil 40 of the objective optical system 18. Thus, in the present embodiment, the thickness of the front cover 16 is substantially uniform within the central region as well as in the periphery. Furthermore, the vicinity of the periphery of the field of view is designed such that, by setting the radius of curvature of the external surface Rp to be a value smaller than Ri and Ro, a smooth joining of the transparent cover 16 with the external diameter portion of the capsule is achieved. In the present embodiment, Rp=4.0 mm. Further, the external diameter D of the capsule endoscope 3 is 11 mm.

In addition, a conic portion of the front surface of the first lens frame 20 is provided with an anti-reflection function by modifying its surface so as to have a generally rough surface 41.

In the present embodiment, the angle θ of the field of view is in the range from 90° through 110°. With the above-mentioned construction, the capsule endoscope can be a smaller size as compared to the case where the radius of curvature in the vicinity of the periphery of the field of view is the same as the radius of curvature of the center of the field of view. If the radius of curvature in the vicinity of the periphery of the field of view is designed to be the same as the radius of curvature of the center of the field of view of the front cover, the external diameter becomes larger and the capsule endoscope becomes enlarged, making it difficult to swallow the capsule endoscope, and/or decreasing the movability of the capsule endoscope.

By having the structure of the present embodiment, the swallowing properties of the capsule endoscope are, improved, and concurrently, smooth mobility of the capsule is enhanced. More specifically, in the case of the present embodiment, the external diameter D (=11 mm) can be smaller than two times the radius of curvature of the external surface Ro (=6.5 mm) in the vicinity of the center of the field of view of the front cover 16. If the radius of curvature in the vicinity of the periphery of the field of view is the same as the radius of curvature of the center of the field of view, the external diameter D becomes 13 mm, making the capsule larger than in the present embodiment.

Figure 3:
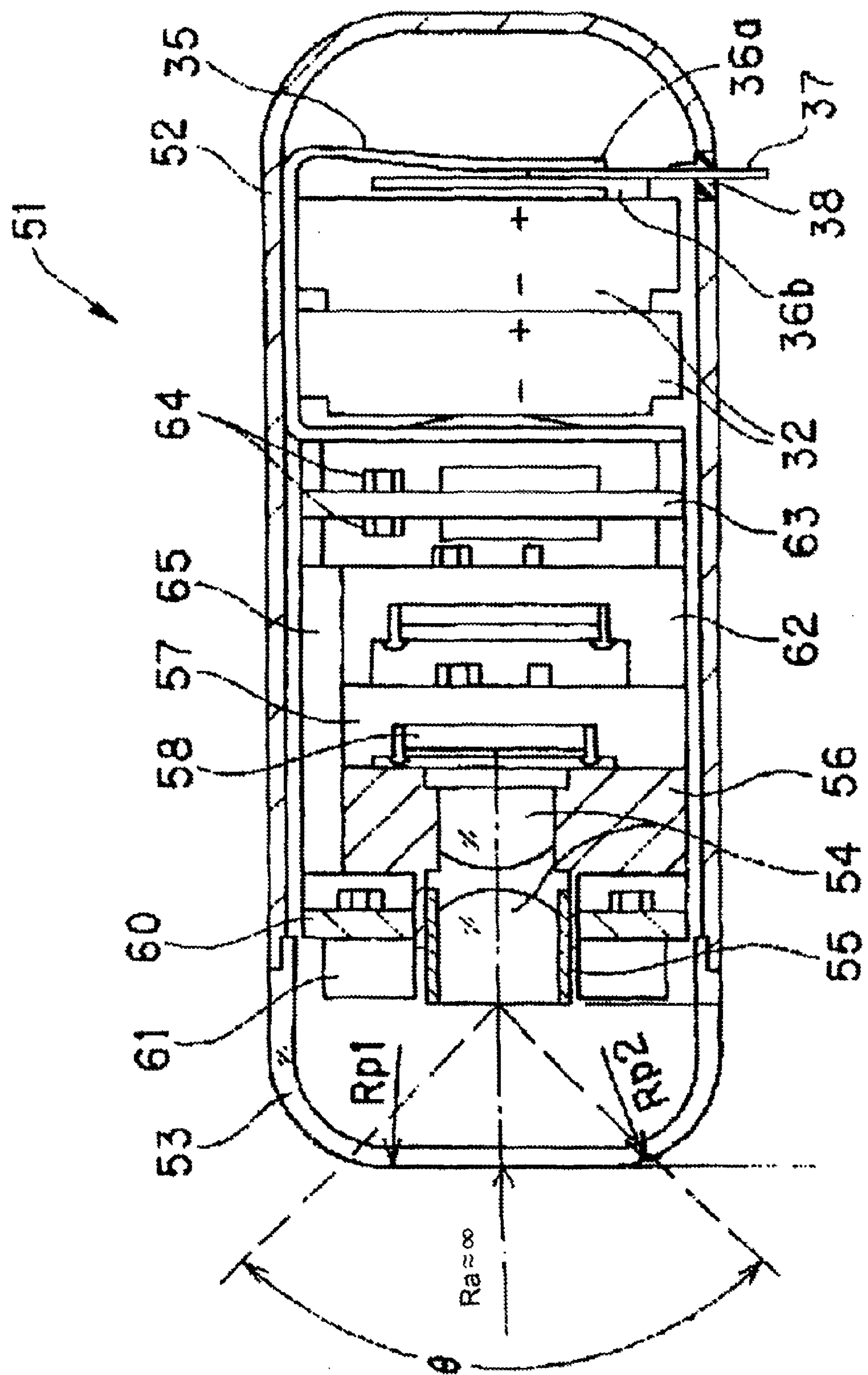
FIG. 3 is a cross-sectional view of a capsule endoscope according to Embodiment 2.

In considering the case where the radius of curvature Ra is nearly equal to infinity (i.e., the front surface is substantially planar in the central region), as shown in FIG. 3, if the radius of curvature in the vicinity of the center of the field of view is designed to be greater than the radius of curvature in the vicinity of the periphery of the field of view, the design results in the restraint of the projection distance of the front cover in the vicinity of the center of the field of view, and enables shortening of the entire length of the capsule endoscope and improving the swallowing properties.

Therefore, the present embodiment is effective in reducing the external diameter and the entire length of a capsule endoscope and in improving the ease of swallowing.

Embodiment 2

FIG. 3 shows Embodiment 2 of the present invention. In the capsule endoscope 51, a transparent front cover 53 engages with the front end of an exterior cover 52, which is a cylinder having a closed rear end that is rounded at the periphery and occluded. The transparent front cover is adhered to the exterior cover 52 so the inside is a watertight structure, and an objective optical system 54 is positioned inside the capsule so as to receive light that transmits through the front cover.

The objective optical system 54 is formed by attaching a first lens and a second lens to a first lens frame 55 and a second lens frame 56, respectively, and is arranged in a center position to the rear of the transparent cover 53. A CMOS image detector 58 is arranged at the image surface of the objective optical system 54. The CMOS image detector 58 is mounted in a centrally located recess that is established in the front surface of a substrate 57 and the second lens frame 56 is engaged with the first lens frame 55.

A substrate 60 is engaged with a cylindrical portion of the second lens frame 56, and both are secured using an adhesive. Plural LEDs 61 that emit white light may be attached to the substrate 60. Further, a substrate that forms a drive processing and memory circuit 62 is arranged on the rear surface of the substrate 57 where the CMOS image detector 58 is attached. In addition, a substrate that includes a radio wave communication circuit 63 is arranged on the rear surface of the substrate. Chip components 64, 64 are mounted on both surfaces of the substrate, and two button-shaped cell batteries 32, 32 are arranged on the rear surface side of the substrate that includes the radio wave communication circuit 63.

Figure 2:
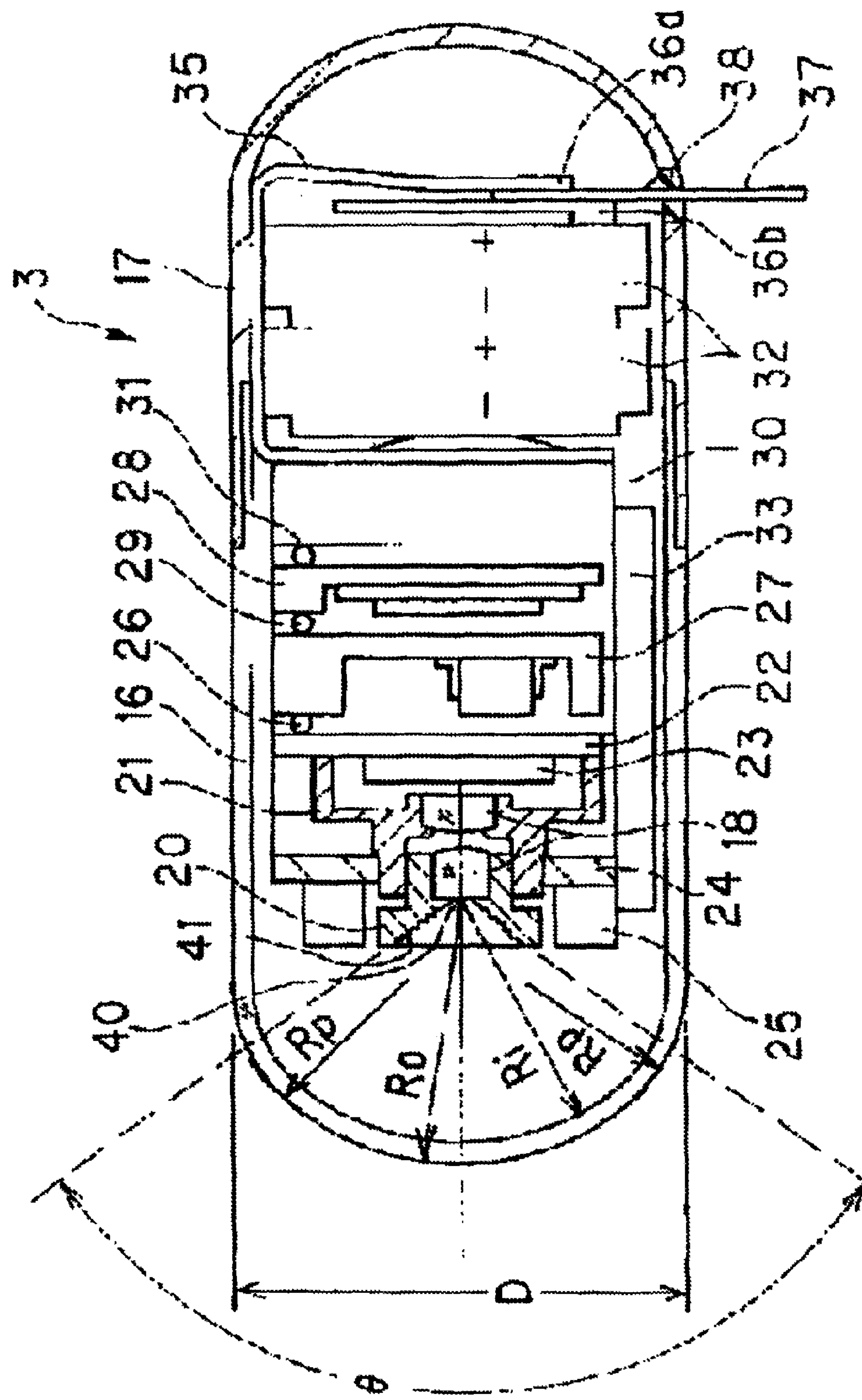
FIG. 2 is a cross-sectional view of a capsule endoscope according to Embodiment 1.

Further, an antenna 65 is arranged on the inside of the capsule next to the substrate that includes the drive processing aid memory circuit 62, and the antenna 65 is connection to the radio wave communication circuit 63. Similar to the explanation made with reference to FIG. 2, batteries 32, 32 are connected with the spring contact point member 35, and set to the OFF state by interposing the insulating string member 37 between the contact point sections 36*a* and 36*b*. Pulling out the string member 37 results in contact being made between the contact point sections 36*a* and 36*b*, thereby setting the ON state. In addition, a valve portion 38 is closed and the sealed state is established and maintained.

In the present embodiment, in a central region of the transparent cover, the internal surface and the external surface of the transparent cover 53 are substantially planar within a central region located on the cylinder axis of the capsule up to the vicinity of the culled peripheral portion. This substantially planar region of the transparent cover includes the range of the field of view of the objective optical system 54. Therefore, the radius of curvature Ra in this central region is nearly equal to infinity. Furthermore, the field of view θ in this central region is in the approximate range of θ=90° through 110°.

By setting the radius of curvature of the transparent cover in a peripheral region that is outside of the field of view of the objective optical system such that the cross-sectional curvature radii Rp1 and Rp2 are smaller than Ra, a smooth joining of the transparent cover 53 with the external diameter portion of the capsule is achieved.

In the present embodiment, the curvature radii Rp1 and Rp2 are set, for example, within the range of 1 mm through 5 mm. Furthermore, the thickness of the transparent cover 53 within the field of view, as well as in the peripheral region, is made to be uniform in the present embodiment, just as is the case for Embodiment 1.

As mentioned above, by forming the center portion of the transparent cover as a substantially planar region within the range of the field of view of the objective optical system enables the forward projection distance of the transparent cover to be reduced and thus shortens the overall length of the capsule endoscope 51. Therefore, the swallowing properties of the capsule endoscope of this Embodiment are improved as compared to Embodiment 1.

Embodiment 3

Figure 4A:
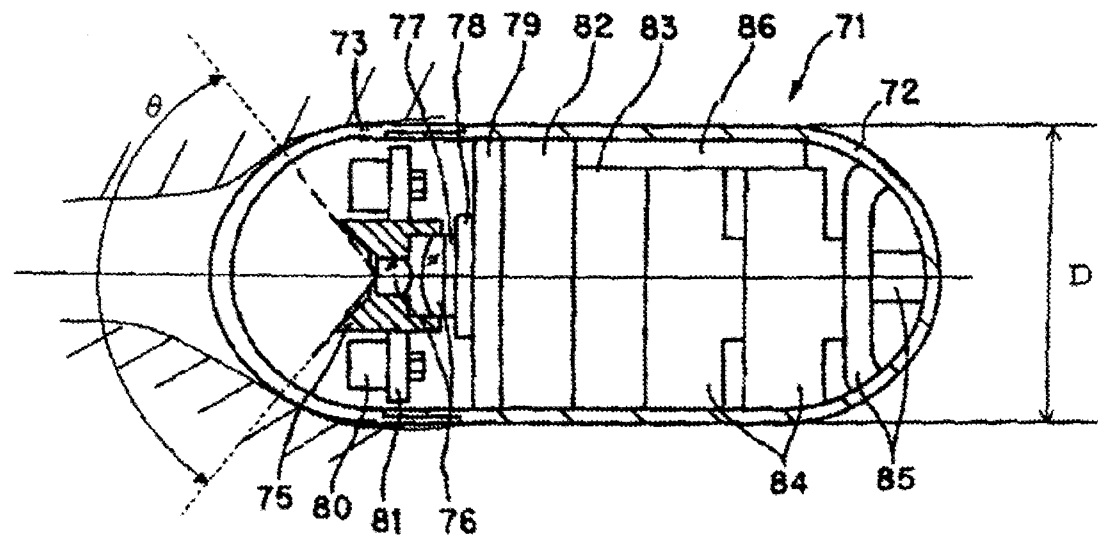
FIGS. 4(*a*) and 4(*b*) are cross-sectional views of a capsule endoscope according to Embodiment 3.
Figure 4B:
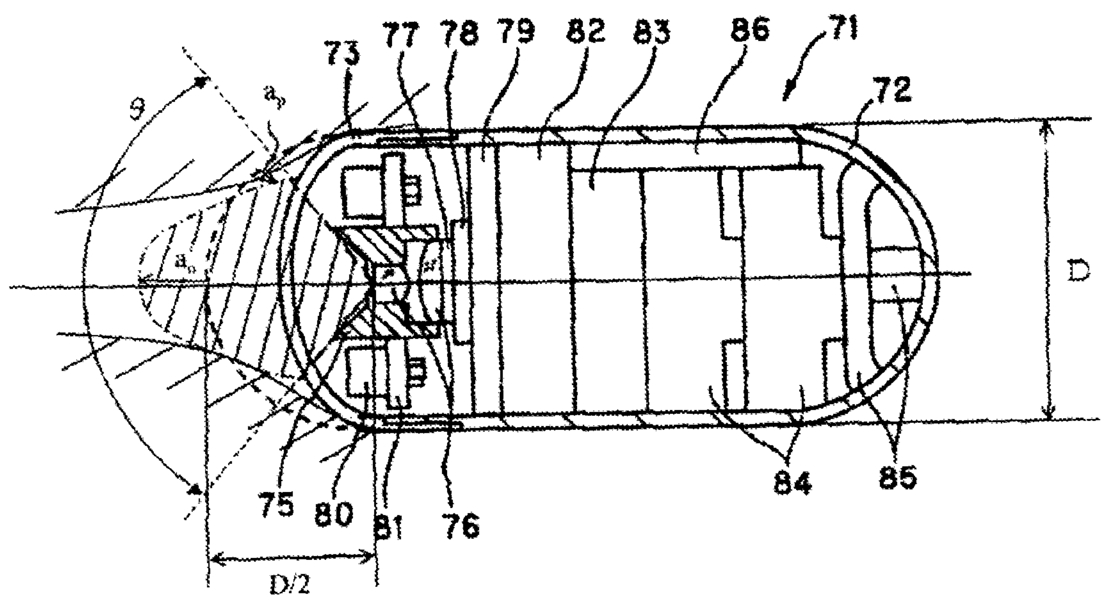

In the capsule endoscope 71 shown in FIG. 4(*a*), a roughly hemispherical transparent cover 73 is connected and secured to an exterior case 72, which comprises a cylinder having an occluded rear portion that is substantially hemispherical and is sealed to the transparent cover 73 so as to be watertight. In the capsule endoscope shown in FIG. 4(*b*), the configuration of the transparent cover 73 has been modified such that the radius of curvature of a portion where a light ray from the periphery of the field of view of the objective optical system 76 passes through is smaller than the radius of curvature of a portion where a light beam from the center of the field of view passes through. In each of the capsule endoscopes shown in FIGS. 4(*a*) and 4(*b*), there is provided within the sealed capsule the below-mentioned components.

An objective optical system 76 that is attached to a lens frame 75 is centrally positioned about the cylinder axis within the capsule so as to receive light that passes through the transparent cover 73.

A CMOS image detector 78 that is protected by a cover glass 77 is arranged at the image surface of the objective optical system 76. The CMOS image detector 78 is mounted to the front surface of a substrate 79. Furthermore, a CCD image detector may be used in lieu of using a CMOS image detector.

Further, the objective optical system 76 is formed of two plano-convex lenses, and the rear surface of the plano-convex lens at the image side is adhered or secured to the cover glass 77.

In the case of performing a focus adjustment in the manufacturing process, the lens frame 75, which has an internal diameter that engages with the external diameter of a piano-convex lens that is the lens positioned within the objective optical system 76 nearest the object side, is adjusted by moving it in a direction along the optical axis relative to the plano-convex lens nearest the image side. After adjustment, the lens and the lens frame 75 are secured using an adhesive. Further, a substrate 81 is secured in place by engaging an aperture thereof, established at the center of the substrate, to a surface that forms the outer diameter of the lens frame 75.

One (or more) white LED(s) 80 may be attached to the substrate 81. Integrated circuit chips and other electrical components are mounted to the substrate 81, thereby forming a drive circuit so as to intermittently energize the white LED 80. In addition, a substrate that forms a drive and processing circuit 82 is arranged on the rear surface of the substrate 79 where the CMOS image detector 78 is attached.

The CMOS image detector 78 is driven by electronic components mounted on the substrate 79 so that image data output signals are obtained. A substrate that includes components which form a radio circuit 83 that transmits image data signals via radio waves is arranged on the rear surface of the substrate that includes a drive and processing circuit 82. Button-shaped batteries 84, 84 are arranged on the rear surface of the substrate that supports the radio circuit 83.

Switches 85, 85 that enable the power to be turned ON from outside the capsule are contained at the rear surface side of the button-shaped batteries 84, 84 and within the rear end of the capsule body. Further, an antenna 86 is located inside the capsule adjacent the radio circuit 83 and the batteries 84, 84. In order to study the optimum depth of field for the capsule endoscope using the present embodiment, the relationship between the capsule endoscope and the internal wall of a hollow internal organ, such as in the digestive tract, will now be discussed.

A capsule endoscope is different from a conventional endoscope in that there is no capability to supply air into an internal organ that is to be observed. Consequently, there is concern that the inside of the digestive tract, which is the usual route for a capsule endoscope, may be contracted thereby blocking the field of view of the capsule endoscope. Further, if the movement of the capsule endoscope within a living body is caused by the peristaltic movement of hollow internal organs, it is assumed that the capsule endoscope will have pressure that is applied by the internal walls of the hollow internal organs to move it forward within the hollow internal organ. Under these conditions, the action at the front end of the capsule to push and widen the internal walls depends upon the external diameter D of the capsule endoscope, as will now be discussed.

FIG. 4(*a*) shows a capsule endoscope 71 that includes the transparent cover 73 that is nearly hemispherical in shape with a radius of curvature R equal to the external diameter D of the capsule endoscope 71 divided by 2, and shows the hollow internal wall around the periphery of the transparent cover 73. Because the hollow internal wall is stably adhered to the external surface of the capsule that includes the transparent cover, the wall surface of the internal organ is located in the vicinity of the surface of the transparent cover at the periphery of the field of view. However, the internal wall must inherently separate from the surface of the transparent cover as one proceeds toward the center of the field of view.

In the capsule endoscope 71 shown in FIG. 4(*b*), the configuration of the transparent cover has been modified relative to that shown in FIG. 4(*a*) so that the radius of curvature in a portion that corresponds with the periphery of the field of view is smaller than the radius of curvature in a portion that corresponds with the center of the field of view. Thus, as is apparent from viewing FIG. 4(*b*), as one approaches the center of the field of view from the periphery of the field of view, the hollow internal wall becomes greatly separated as compared to a hypothetical spherical surface of radius of curvature R equal to the capsule external diameter D divided by 2, which is indicated in FIG. 4(*b*) by the line formed of dashes. In the case where the transparent cover has a hemi-spherical shape, it may be considered that the internal wall of the hollow internal organ in the region just forward of the periphery of the field of view conforms in shape to the transparent cover, and thus the internal wall of the hollow internal organ will be spherical near the periphery of the field of view.

Progressing toward the center of the field of view, the hollow internal wall of the internal organ must inherently become greatly separated from the transparent cover. Consequently, where a transparent cover has a substantially hemispherical surface of radius of curvature R equal to the capsule external diameter D divided by 2, the subject surface for observation near the periphery of the field of view will be assumed to be a spherical shape by reason of coinciding in shape with that of the hemispherical transparent cover near the periphery of the field of view.

According to the above, in order to perform observations with a capsule endoscope without failing to notice lesions, it becomes necessary that a substantially spherical surface of radius of curvature R equal to the external diameter D of the capsule divided by 2 be maintained within the depth of field at the periphery of the field of view. And concurrently it becomes necessary that a sufficiently distant object is also within the depth of field in the center of the field of view.

However, in the usual objective optical system where the curvature of field has been corrected, there is not much difference in the depth of field at the center of the field of view versus at the periphery of the field of view. Therefore, in a capsule endoscope using such a usual objective optical system, it is difficult to provide a sufficient depth of field over the entire viewing range. This point shall be additionally explained in detail with reference to FIG. 7(*a*).

Figure 7A:
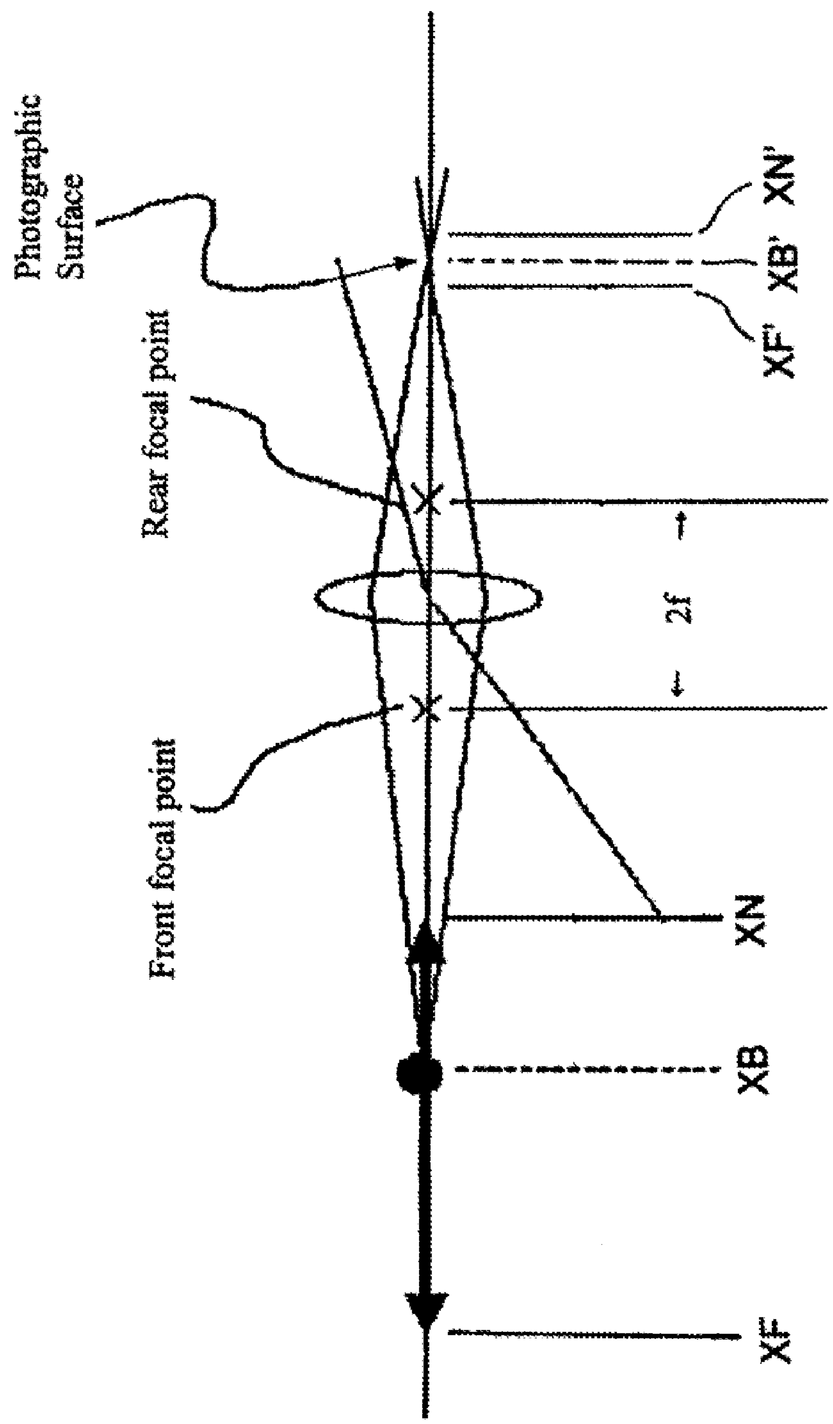
FIGS. 7(*a*) and 7(*b*) are explanatory diagrams that illustrate the depth of field and the image surface when a spherical surface is regarded as the object.
Figure 7B:
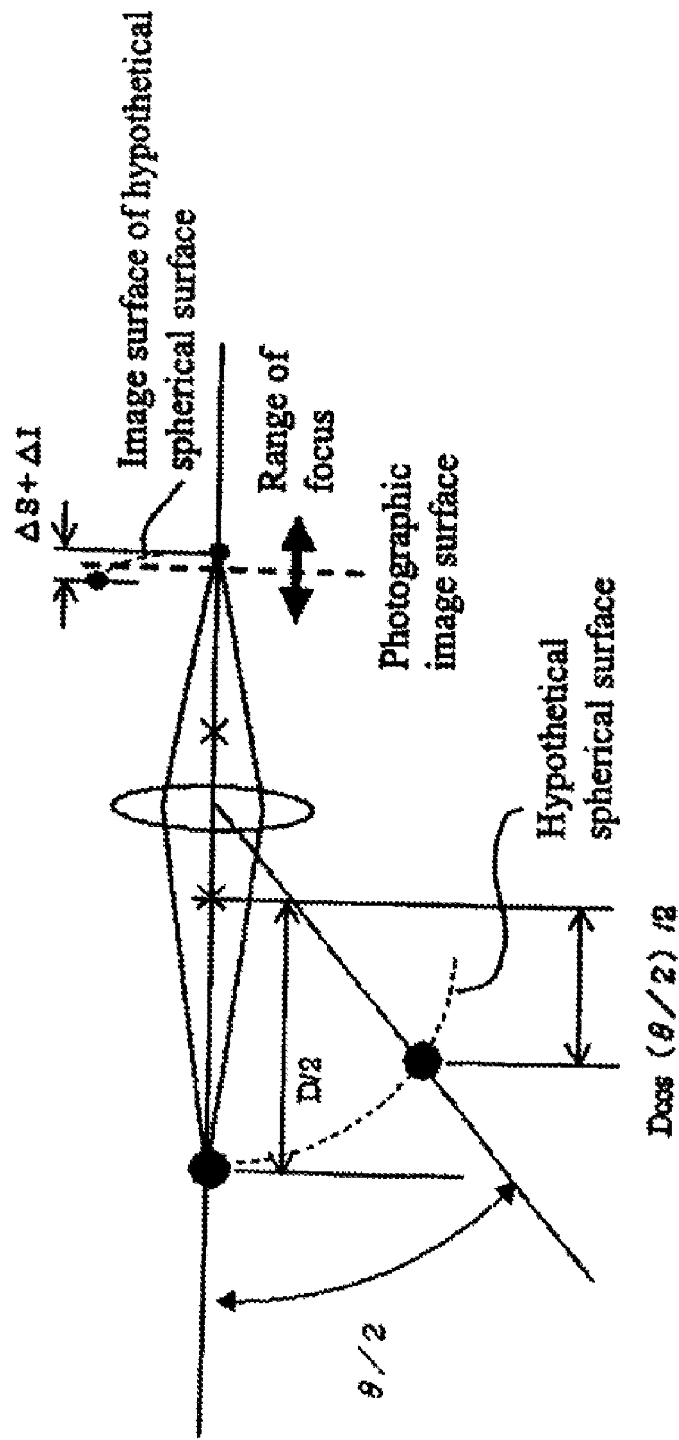

Referring to FIG. 7(*a*), a case is considered for a general capsule endoscope where a solid-state image pickup device having a pixel pitch p (in linear units) is arranged at an image plane position XB' for capturing images, with the 'best focus' position for the image plane of the objective optical system being regarded as XB. When an object approaches the position MN in the state where the solid-state image pickup device is fixed, the image plane shifts from the position XB' to the position XN'. However, when the diameter of a permissible circle of confusion at the image plane is smaller than the resolution K·p (where K is a coefficient that is determined by the characteristics of the solid state image pickup device and the circuit(s)) of the solid state image pickup device, it can be considered such that an image of an object situated within the range from the position XB to the position XN is 'in focus'. In other words, the range where the diameter of the permissible circle of confusion becomes K·p or less can be defined as the depth of field at the near point.

At this time, the following Equation (B) applies according to Newtons image formation expression:

$$1/XN-1/XB=K\cdot p\cdot Fno/f^2 \qquad \text{Equation (B).}$$

Similarly, an expression for the depth of field at the far point side may also be defined as follows:

$$1/XB-1/XF=K\cdot p\cdot Fno/f^2 \qquad \text{Equation (C).}$$

By adding Equations (B) and (C), the following equation is obtained:

$$1/XN-1/XF=2\cdot K\cdot p\cdot Fno/f^2 \qquad \text{Equation (D)}$$

where

XB is the distance from the front focal position to the 'best focus' position of the objective optical system;

XN is the distance from the front focal position to the near point of the depth of field of the objective optical system;

XF is the distance from the front focal position to a far point of the depth of field of the objective optical system, f is the focal length of the objective optical system; and Fno is the F-number of the objective optical system.

The Equations (B)-(D) above are general expressions that apply for paraxial rays. However, these equations also apply for off-axis rays under conditions where curvature of field of the objective optical system has been made sufficiently small.

Figure 5B:
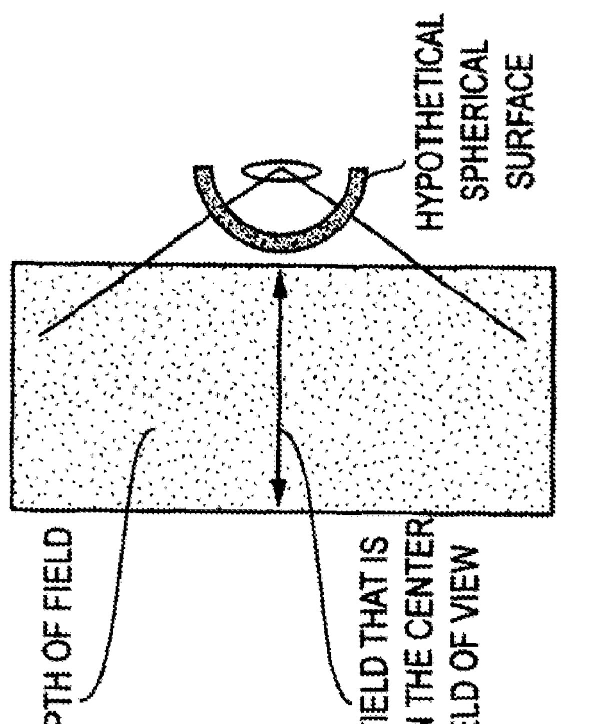
FIGS. 5(*a*) and 5(*b*) are schematic diagrams that are used to explain tradeoffs in selecting the depth of field where the curvature of field has been sufficiently corrected.
Figure 5A:
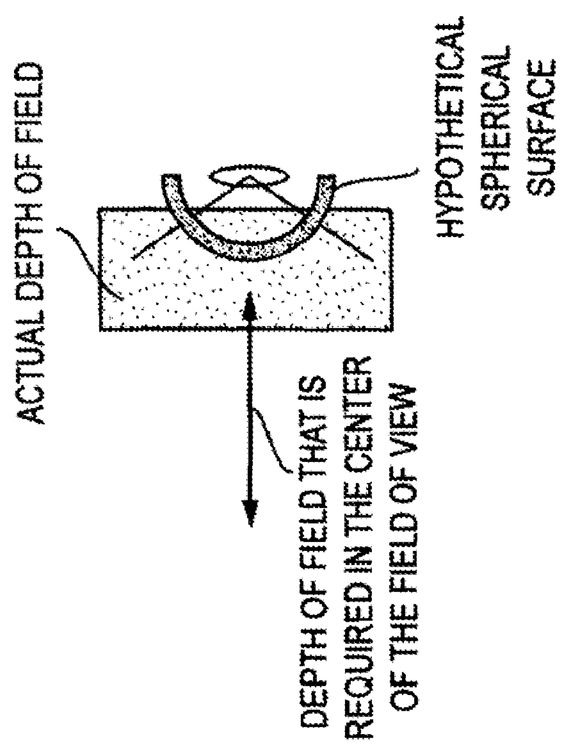

FIGS. 5(*a*) and 5(*b*) are diagrams that show the depth of field that can be obtained in an objective optical system where the curvature of field has been corrected so as to form substantially planar surfaces.

In a capsule endoscope having an external diameter D in the approximate range of several mm through 10 mm, the distance from the objective optical system to a hypothetical spherical surface is very short. Consequently as shown in FIG. 5(*a*), which illustrates the situation of using an objective optical system where the curvature of field has been sufficiently corrected, if a hypothetical spherical surface is established to be within the depth of field at the periphery of the field of view, the depth of field at the far point in the center of the field of view becomes insufficient to observe an object (e.g. the internal wall) at the center of the field of view. On the other hand, as shown in FIG. 5(*b*), when a sufficient depth of field at the far point in the center of the field of view is attempted to be obtained so as to view an object at the center of the field of view, a hypothetical spherical surface cannot be situated within the depth of field near the periphery of the field of view.

In order to increase the depth of field, there is a well known technique to accomplish this that restricts the aperture of brightness diaphragm, resulting in an increase of the F-number. However, using such a technique, a sufficient brightness for the observation of an object cannot be obtained.

Therefore, in order to achieve suitable observations for a capsule endoscope, an objective optical system is needed wherein the range of the depth of field is different, depending upon the angle of view.

In other words, an objective optical system for a capsule endoscope may be constructed that maintains a hypothetical or real, substantially spherical surface within the depth of field for viewing angles that correspond to the periphery of the field of view, and concurrently, provides a sufficient depth of field at the far point side for viewing angles in the range from the center of the field of view to a position between the center of the field of view and the periphery of the field of view. This can be achieved by adopting an objective optical system wherein curvature of field of the image surface has been intentionally generated, and by appropriate adjustment of the focus of the objective optical system.

FIG. 6(*a*) shows the range of the depth of field in the case of changing the depth of field depending upon the angle of view. The thick solid line indicates a hypothetical spherical surface, and the thick dotted line indicates the internal wall of an organ in the case of using a capsule endoscope within a hollow internal organ.

FIG. 6(*b*) shows the situation where the object surface has the same shape as the hypothetical spherical surface. In this case, only the periphery of the object is within the depth of field and may be clearly observed, but the center region of the field of view blurs.

FIG. 6(*c*) shows the situation where the object of interest is the internal wall. In this case, both the periphery and the center of the field of view are within the depth of field and thus an object may be clearly observed over the entire range of the field of view.

Setting the range of the depth of field as shown in FIG. 6(*a*) enables obtaining an excellent observation state that includes from the center of the field of view to the periphery of the field of view within the depth of field.

In order to achieve the depth of field as shown in FIG. 6(*a*), it is necessary to purposefully generate a large curvature of field wherein, the higher the image height becomes, the greater the image surface tilts toward the object side, becoming a concave image formation surface that is orientated toward the object side when a hypothetical spherical surface is regarded as the object to surface.

FIG. 7(*b*) is an explanatory diagram that shows the configuration of the image surface formed by the objective optical system, and that shows focusing of the imaging unit when a hypothetical spherical surface of radius of curvature R that is equal to the external diameter D of the capsule endoscope divided by 2 is regarded as the object. As used in the preceding sentence, 'focusing' is an operation to determine the position of the image receiving surface by shifting the image receiving surface, in a direction that is parallel to the optical axis, so as to obtain the necessary depth of field.

When a hypothetical spherical surface is regarded as the object, and when the image surface of the objective optical system has concave orientation toward the object side, if focusing is performed so that a transparent cover having a hypothetical spherical surface is situated within the depth of field at the periphery of the field of view, the image receiving surface of a solid-state image pickup device shifts toward the object side as measured from a conjugate, on-axis point of the hypothetical spherical surface.

In general, an objective optical system of an endoscope forms an image by reducing the scale of the image relative to the scale of the object, so a shifting of the image surface is projected toward the object side in a magnified scale. Therefore, if the position of the image surface is slightly shifted, the conjugate point of the image surface on the object side greatly shifts away from the transparent cover. Therefore, it becomes possible to achieve the depth of field shown in FIG. 6(*a*).

In an objective optical system that has a wide angle of view, the front end surface of the objective optical system and an entrance pupil substantially coincide.

Further, in a capsule endoscope, because the front end surface of the objective optical system is located in the vicinity of the center of curvature of the hypothetical spherical surface, the relationship between the amount of curvature of field that is generated by the objective optical system and the focusing of the imaging unit (i.e., shifting of the image surface) can be expressed using the below Equations (E)-(G).

When a hypothetical spherical surface of radius of curvature R equal to the external to diameter D of the capsule endoscope divided by 2 is regarded as the object, and the optical distance on the axis from the front end surface of the objective optical system to the hypothetical spherical surface is established as D/2, the difference Δs of the image position due to a difference in the object points on the optical axis and the maximum image height is given by the following equation:

$$\Delta s = Z_E' - Z_0' = 2f^2(1-\cos(\theta\max/2))/(D\cdot\cos(\theta\max/2)) \quad \text{Equation (E)}$$

where $Z_0'$ is the image position on the optical axis, which can be expressed as the following Equation (F):

$$Z_0' = f^2/(D/2+f_F) \quad \text{Equation (F)}$$

where f and D are as defined previously, and $f_F$ is the front focal distance.

$Z_E'$ is the image position at the maximum image height (i.e., at the maximum half-field angle (θmax/2)), which can be expressed as the following Equation (G):

$$Z_E' = f^2/[D/2\cdot\cos(\theta\max/2)+f_F] \quad \text{Equation (G)}$$

where f, D, θmax/2, and $f_F$ are as defined previously.

It should be noted that, in Equation (G), $f_F \ll D$.

When a hypothetical spherical surface is regarded as the object, for the purpose of the image surface of the objective optical system having a concave orientation toward the object side, the following Condition (6) applies:

$$\Delta s + \Delta I \leqq 0 \quad \text{Condition (6)}$$

where

ΔI is the amount of curvature of field at the maximum image height.

Thus, the above Condition (1) can be achieved due to the generation of a large astigmatism even if the Petzval sum in the objective optical system is small. However, if the astigmatism is excessively large, the astigmatic difference (meaning the distance between the sagittal image surface S and the tangential image surface T) also becomes greater in the region of the third-order aberration, and it becomes difficult to secure excellent observation performance to near the periphery of the field of view when viewing a surface region having a spherical shape.

In this situation, the manner in which Condition (1) above can be satisfied without generating excessive astigmatism will be considered next.

When the astigmatism is very small, because it is considered that the ΔI in Condition (1) above will equal the amount of curvature of field that is known as the Petzval curvature, it can be established that $$\Delta I = -IH\max^2\cdot P \leqq 0 \quad \text{Condition (7)}$$

where

IHmax and P are as defined above.

In this situation Condition (1) becomes as follows:

$$2f^2\{1-\cos(\theta\max/2))\}/D\cdot\cos(\theta\max/2) - IH\max^2\cdot P \leqq 0 \quad \text{Condition (8)}$$

which can be rewritten as Condition (5) above.

If Condition (5) above is not satisfied, it is necessary to generate astigmatism and to satisfy Condition (1) above, making it difficult to secure an excellent observation performance near the periphery of the field of view upon viewing a surface portion having a spherical shape.

Further, the term IHmax/f in Condition (2) above can almost be determined when the maximum angle of view is determined, as shown in the explanation of Condition (2), as will be discussed later.

Therefore, if the maximum angle of view and the external diameter D of the capsule endoscope are determined, a necessary Petzval sum P can be estimated rising the above Condition (5).

The above Conditions (1) and (5) clarify the minimum requirement in the amount of curvature of field of the objective optical system in order to obtain the optimum observation region for the capsule endoscope.

In an actual capsule endoscope, the necessary amount of curvature of field shall be determined according to the depth of field that is needed in the center of the field of view, an achievable F-number, and the general performance of the image pickup device.

In the region from the center of the field of view up to an intermediate position between the center and the periphery of the field of view, it is necessary to secure a depth of field of the same amount as needed in the center of the field of view.

Therefore, when a plane that is placed in the 'best focus' position in the center of the field of view (determined according to focusing), is regarded as the object, it is desirable that an image formation surface that is conjugate with the object coincide with the image surface.

However, in actuality, because image surface curvature (i.e., Petzval image curvature) determined according to the Petzval sum, is generated, an astigmatism is generated in order for the image surface to become closer to the image receiving plane.

Figure 8B:
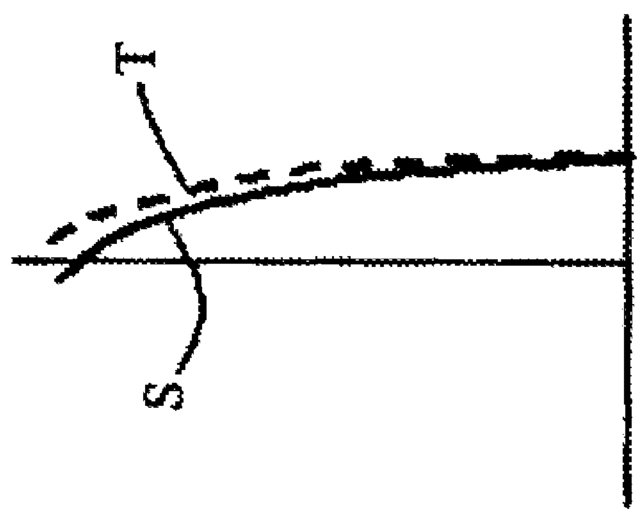
FIG. 8(*a*) is a diagram that shows the relationship of the sagittal image surface S and the tangential image surface T relative to the image receiving surface of an image pickup device when a plane that is placed in the 'best focus' position in the center of the field of view is regarded as the object after focusing has been performed.
Figure 8A:
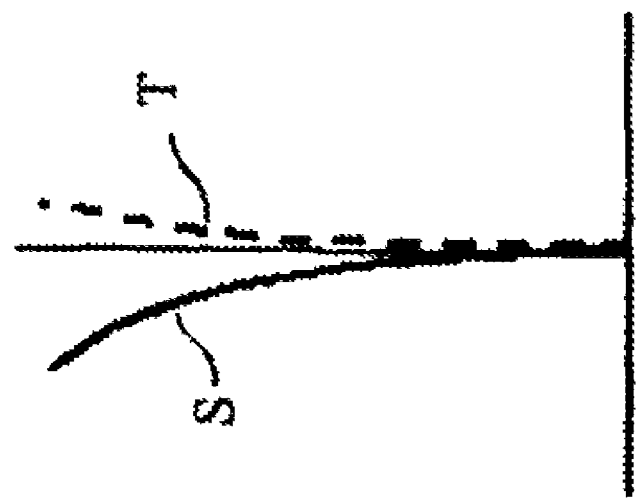

FIG. 8(*a*) is a diagram that shows the relationship of the sagittal image surface S and the tangential image surface T relative to the image receiving surface (the vertical line) of an image pickup device when a plane that is placed in the 'best focus' position in the center of the field of view is regarded as the object after focusing has been performed. As shown in FIG. 8(*a*), in the third-order aberration region, the higher the image height, the greater the astigmatic difference. However, as long as the astigmatic difference from the optical axis to the intermediate image height is sufficiently corrected, a significant problem does not arise since the image receiving surface remains near the average position of the S and T image surfaces.

FIG. 8(*b*) is a diagram that shows the relationship of the sagittal image surface S and the tangential image surface T relative to the image receiving surface (the vertical line) of an image pickup device when a spherical surface region near the periphery of the field of view is regarded as the object after focusing has been performed. When a substantially spherical surface region is regarded as the object near the periphery of the field of view, the astigmatic difference will be sufficiently corrected when the above Condition (5) is satisfied. Such a design enables excellent observation performance to be obtained from the center of the field of view to the periphery of the field of view.

In addition, with a capsule endoscope, it is difficult to control the direction of observation; thus it is helpful to provide a wide angle of view. In order to secure a sufficient illumination light intensity at the periphery of the field of view, in general, a relationship between the image height IH and the angle view is established as follows:

$$IH = f \cdot K_d \cdot \sin(\theta / 2K_d) \qquad \text{Equation (H)}$$

where $K_d$ is a coefficient determined by the distortion type.

According to the above relationship, when the maximum angle of view has been determined IHmax/f can be approximately determined.

In order to obtain the minimum angle of view that is desirable for a capsule endoscope, it is necessary to satisfy the above Condition (2). If the maximum image height IHmax becomes insufficient to satisfy the above Condition (2), it becomes difficult to provide a sufficient angle of view.

In the objective optical system described above, the depth of field can be variably established depending upon the focusing of the imaging unit.

Conditions (3) and (4) above are to insure that an appropriate focus adjustment is provided over a viewing range of $\theta/2=40°$ through $\theta max/2$ (i.e., when the half-angle of view $\theta/2$ is measured from the optical axis).

As shown in FIG. 4(*b*), $a_0$ is the distance on the axis of the near point of the depth of field of the objective optical system as measured from a hypothetical spherical surface, and $a_p$ is the distance off the axis of the objective optical system of the near point of the depth of field of the objective optical system as measured from the hypothetical spherical surface. Whereas a single, on-axis, distance is denoted by $a_0$, the distances denoted by $a_p$ change, depending upon the half-angle of view (i.e., the viewing angle as measured from the optical axis). A hypothetical spherical surface (shown with a broken line) is regarded as a reference surface from which the distances $a_0$ and $a_p$ are measured. Directions from the hypothetical spherical surface away from the objective optical system are defined as being positive, and directions from the hypothetical spherical surface toward the objective optical system are defined as being negative.

When the depth of field is established so as to satisfy the above Conditions (3) and (4), the following efficacies can be obtained:

(a) Securing a High Picture Quality at the Far Point

When miniaturization of a capsule endoscope is attempted to be realized, the distance between the objective optical system and a hypothetical spherical surface becomes short. Consequently, if $a_0$ is equal to zero so that a hypothetical spherical surface is at the near point of the depth of field on axis, the distance to the far point of the depth of field on-axis becomes rather short, and no object at a relatively far distance can be observed.

For the purpose of increasing the depth of field, there is a well-known technique that limits the aperture of a brightness diaphragm in the objective optical system and thereby increases the F-number. However, using such a technique is disadvantageous in that the images become too dark. Further, in a capsule endoscope, there are relatively few cases in which an internal wall of a digestive tract makes contact on the optical axis with a hemispherical front transparent surface. Thus, by making the near point of the depth of field, on axis, lie beyond a hypothetical spherical surface at the front of the capsule (i.e., the near point of the depth of field is a positive number) the far point of the depth of field can be made more distant than if the depth of field were made to include a point, on-axis, immediately adjacent the capsule. Thus, a desired depth of field range on the optical axis can be obtained.

(b) Securing a High Picture Quality at the Near Point

Within a living body, at least a portion of an interior wall (i.e., the usual object of interest) that is near the periphery of the field of view is located adjacent the transparent front cover. Therefore, for the purpose of obtaining as much information as possible, it is desirable that a hypothetical spherical surface (i.e., as if the transparent front cover were a hemisphere) be situated within the depth of field of the objective optical system over viewing angles from an intermediate image height up to the maximum image height.

Satisfying Condition (4) above ensures that images of lesions, which may be located near the periphery of the field of view will be within the depth of field of the objective optical system, and thus will likely be detected.

For the purpose of performing a simple examination of whether or not the capsule endoscope satisfies Condition (4), a verification of this Condition being satisfied should be performed as follows:

When the configuration of the transparent cover is nearly that of a hemispherical surface where R=D/2, an object, such as a resolution chart, can be pressed so as to be immediately adjacent the surface of the transparent cover. In this state, it should be confirmed (via images obtained from the objective optical system that are displayed on a monitor) that: (1) at the center of the field of view that is outside of the depth of field, no resolution is realized; and (2) near the periphery of the field of view, good resolution is realized when viewing a substantially spherical surface.

Further, when the configuration of the transparent front cover differs greatly from that of a hemispherical surface, a jig for evaluation that has a hemispherical surface of radius of curvature R equal to the outside diameter D of the capsule divided by 2 can be prepared, and the jig for evaluation can then be arranged so as to establish the optical distance from the objective optical system to the evaluation surface of the jig as a distance D/2, after which a verification process similar to that described above can be performed.

Embodiment 4

Figure 9:
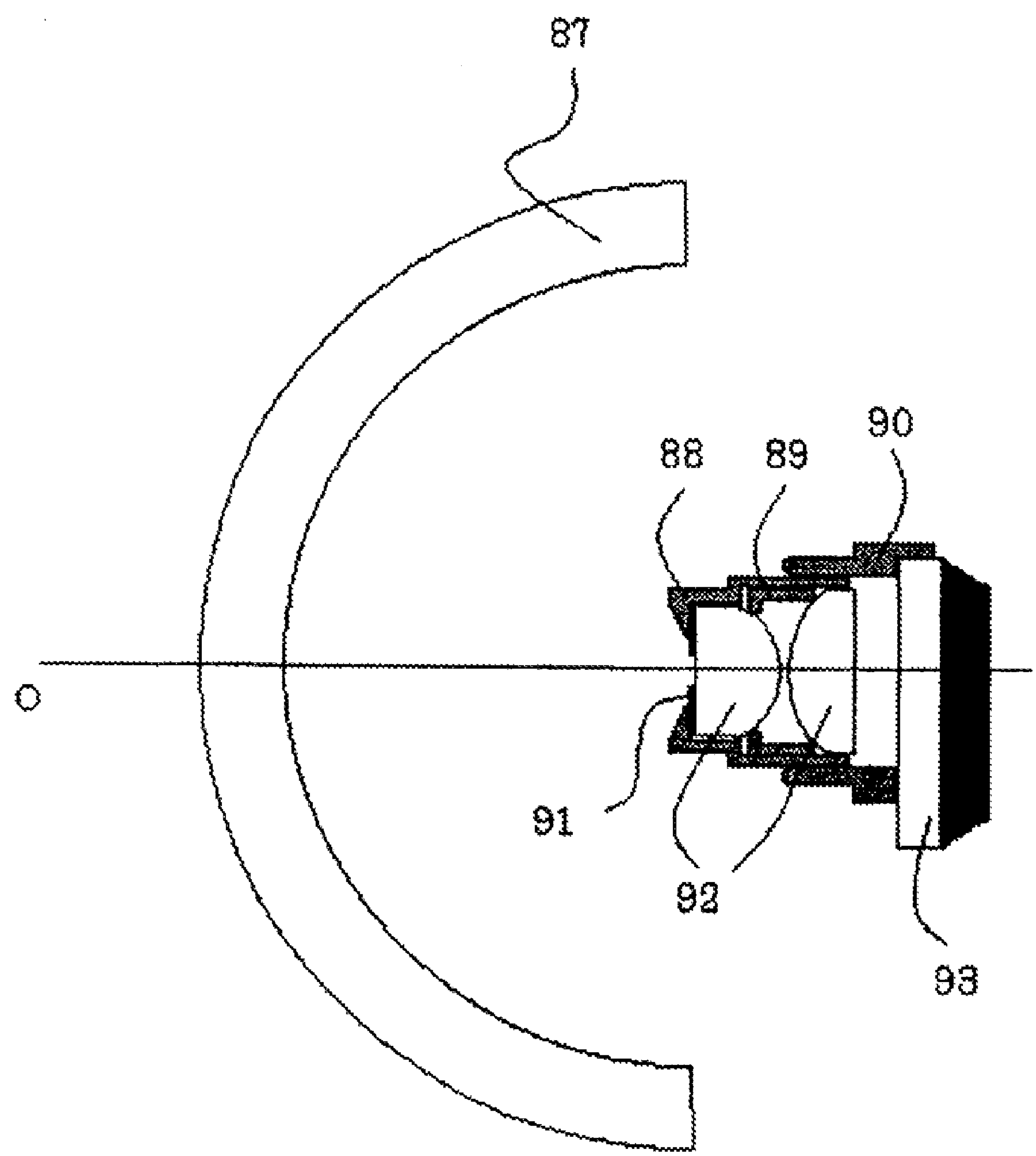
FIG. 9 is a partial cross-sectional view of a capsule endoscope according to Embodiment 4.

FIG. 9 shows Embodiment 4 of the present invention, wherein a transparent cover 87 has a hemispherical configuration, and the radius of curvature of the external surface thereof is 4.5 mm. Consequently, the external diameter of the capsule endoscope is 9 mm. An objective optical system 92, which is attached to a lens frame 88, is arranged so as to be in the state where an entrance pupil of the objective optical system coincides with the center of curvature of the external surface of the transparent cover 87.

A CCD image detector 93, that is secured to a CCD holder 90 using an adhesive, is arranged at the image formation position of the objective optical system.

The objective optical system 92 is formed of two plano-convex lenses, and the interval between the lenses is determined according to a spacer ring 89.

The planar surface of the plano-convex lens that is arranged on the object side of the objective optical system is adhered or secured to the lens frame 88.

Further, since a diaphragm 91 for controlling brightness of the image is arranged a the object-side surface of the objective optical system 92, the object-side of the objective optical system and the entrance pupil position coincide with each other in the objective optical system for the present Embodiment.

In addition, in the case of performing focusing, adjustment is performed by moving the CCD holder 90, which has an internal diameter that engages with an external diameter of the lens frame 88, along the optical axis O direction relative to the lens frame 88. After the adjustment, the CCD holder 90 is secured using an adhesive.

Figure 10:
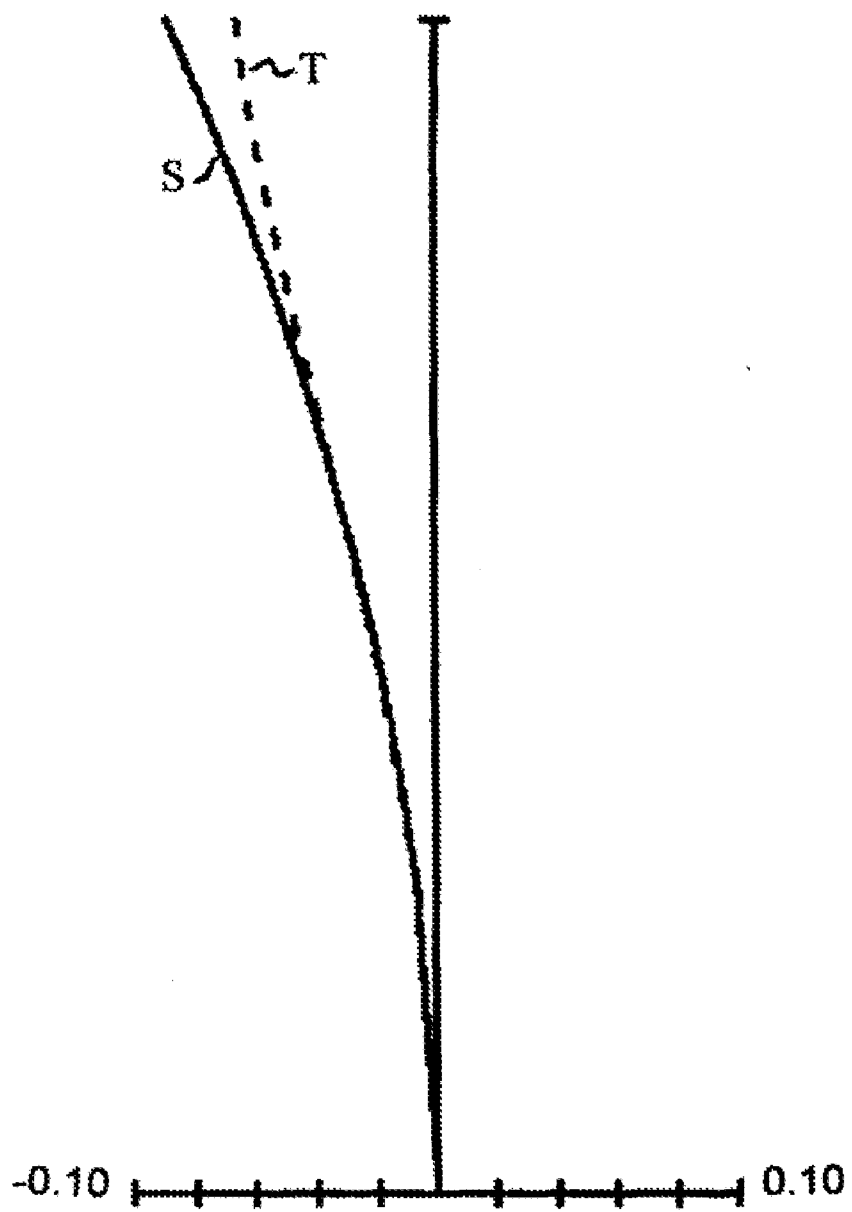
FIG. 10 shows the curvature of field when a spherical surface is viewed using the capsule endoscope according to Embodiment 4.

FIG. 10 shows, for the objective optical system 92 shown in FIG. 9 and when the maximum angle of view is set at 90°, the curvature of field for both the sagittal image surface S and the tangential image surface T in the case of a spherical surface region of radius of curvature R equal to 4.5 mm being regarded as the object. In FIG. 10, the horizontal axis indicates the distance from the paraxial image formation position, and the vertical axis indicates die height of an image. As is apparent from FIG. 10, the image surface of ‘best focus’ (not illustrated, but located midway between the sagittal image surface S and the tangential image surface T) is obviously a concave surface orientated toward the object side.

In Embodiment 4, focusing enables a setting where $a_0$=1.5 mm; the distance from the near point to the far point on the axis is approximately 30 mm; and an, angle of view θ of approximately 60° or more on the surface of the transparent cover is within the depth of field. Therefore, when hollow internal organs are observed, the area from the center of the field of view to the periphery of the field of view will be in focus on the screen, so it is possible to obtain observations without overlooking lesions.

The objective optical system 92 of Embodiment 4 is formed of two plano-convex lenses. In general, two plano-convex lenses are less expensive to manufacture than is a single biconvex lens. Therefore, plano-convex lenses are preferably used for a disposable product such as a capsule endoscope.

Table 1 below lists the performance and construction data for the objective optical system 92 of Embodiment 4. In the top portion of the table are listed the focal length f, the position of the front focal point $f_F$, the position of the back focal point $f_B$, the image height IH, and the field of view θ. In the middle portion of the table, in the left column, are listed the radii of curvature of each surface, starting with the radius of curvature of the surface nearest the object side (r1) and ending with die image surface. In the second column are listed the on-axis surface spacing from the surface having the radius of curvature listed in the left column on the same line to the next surface, in order from the object side. In the third column are listed the index of refraction of the optical material of each lens element. Where no index of refraction is listed in the third column, the optical medium is air, having an index of refraction of unity. In the fourth column are listed the Abbe number of the optical material having the index of refraction as listed in the third column for the same line. The index of refraction ni and Abbe number υi that are listed are relative to the d-line. In the bottom portion of the table are listed the values of interest in calculating Conditions (1), (2) and (5).

TABLE 1 f = 0.914, $f_F$ = −0.339, $f_B$ = −0.078
IH = 0.666, θ = 90.7°, $X_B$ = −10

| | | | |
|---|---|---|---|
| r1 = ∞ (diaphragm) | d1 = 0 | | |
| r2 = ∞ | d2 = 0.9 | n2 = 1.79196 | ν2 = 47.1 |
| r3 = −1.2030 | d3 = 0.1 | | |
| r4 = 1.6970 | d4 = 0.55 | n4 = 1.79196 | ν4 = 47.1 |
| r5 = ∞ | d5 = 0.6235 | | |
| r6 = ∞ (image plane) | d6 = 0 | | |

Values of interest in calculating Conditions (1), (2) and (5):

| | |
|---|---|
| Condition (1) | Because ΔS equals −0.14 and ΔT equals −0.10, \|ΔI\| equals −0.12, and $2f^2$ {1 − cos (θmax/2)}/D · cos (θmax/2) equals 0.08. Therefore, the left-hand side of Condition (1) is such that 0.08-0.12 equals −0.04. |
| Condition (2) | IHmax/f equals 0.73 |
| Condition (5) | Because P equals 0.63, and D equals 9, the right-hand side of Condition (5), i.e., P · D, equals 5.67; the left-hand side of Condition (5), i.e., $2f^2$ {1 − cos (θmax/2)}/$IHmax^2$ · cos (θmax/2) equals 1.56. |

Embodiment 5

Figure 11:
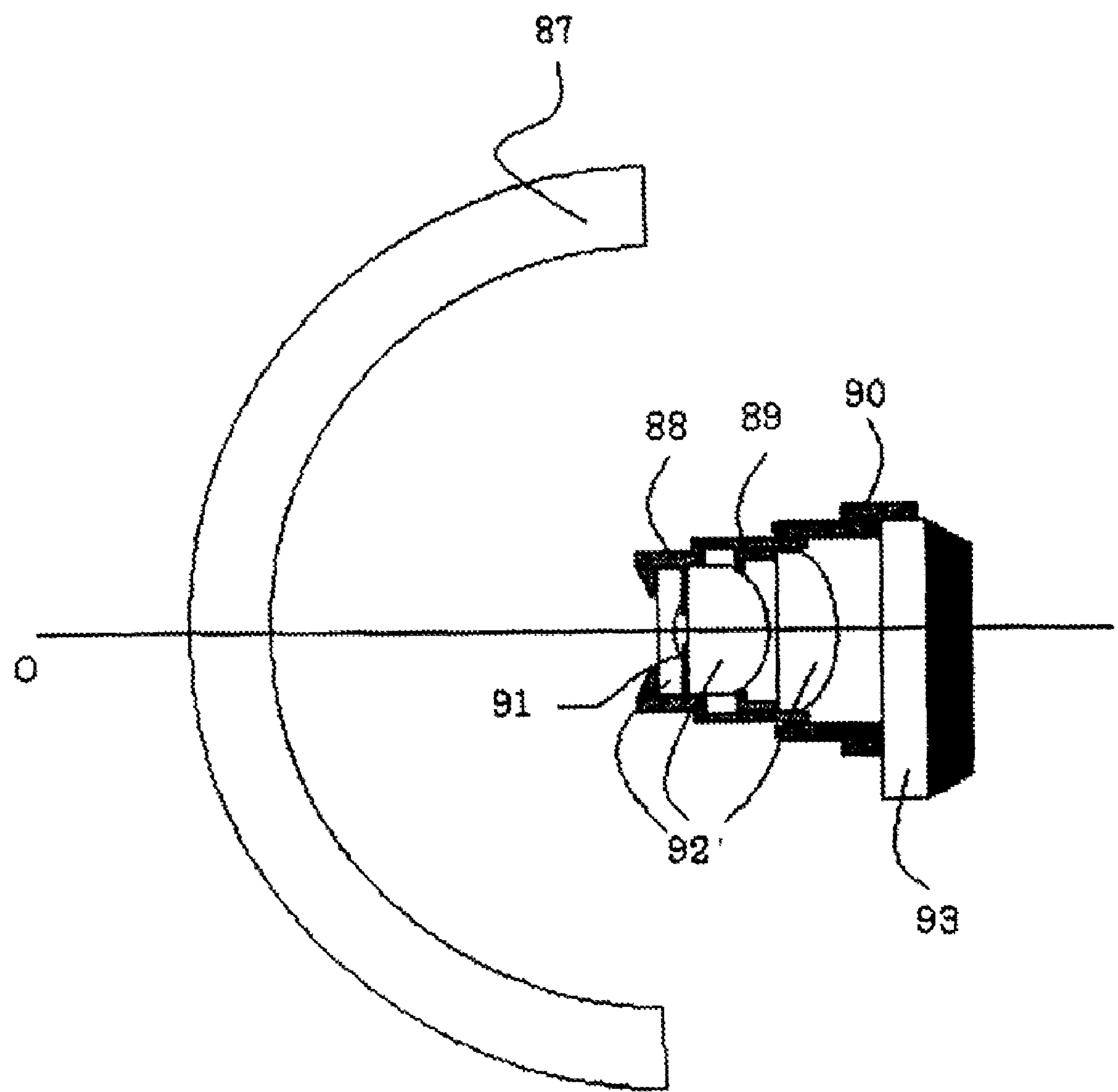
FIG. 11 is a partial cross-sectional view of a capsule endoscope according to Embodiment 5.

FIG. 11 shows Embodiment 5 of the present invention.

The transparent cover 87 has a hemispherical configuration, and the radius of curvature of the external surface is 4.5 mm. Consequently, the external diameter of the capsule endoscope is 9 mm. The objective optical system 92' that is attached to the lens frame 88 is arranged in the center of the capsule and so that the entrance pupil of the objective optical system coincides with the center of curvature of the external surface of the transparent cover 87.

The CCD image detector 93 secured to the CCD holder 90 using an adhesive is arranged at the image formation position of the objective optical system. The objective optical system 92' is comprised of one plano-concave lens and two plano-convex lenses, and the side of the plano-convex lens situated nearest the image side is adhered to the lens frame 88. In the ease of performing focusing, adjustment is performed due to the movement of the CCD holder 90, which has an internal diameter that is engaged with an external diameter of the lens frame 88. The movement of the CCD holder 90 is along the optical axis O direction of the lenses held in the lens frame 88, and after the adjustment, the CCD holder is secured using an adhesive.

Figure 12:
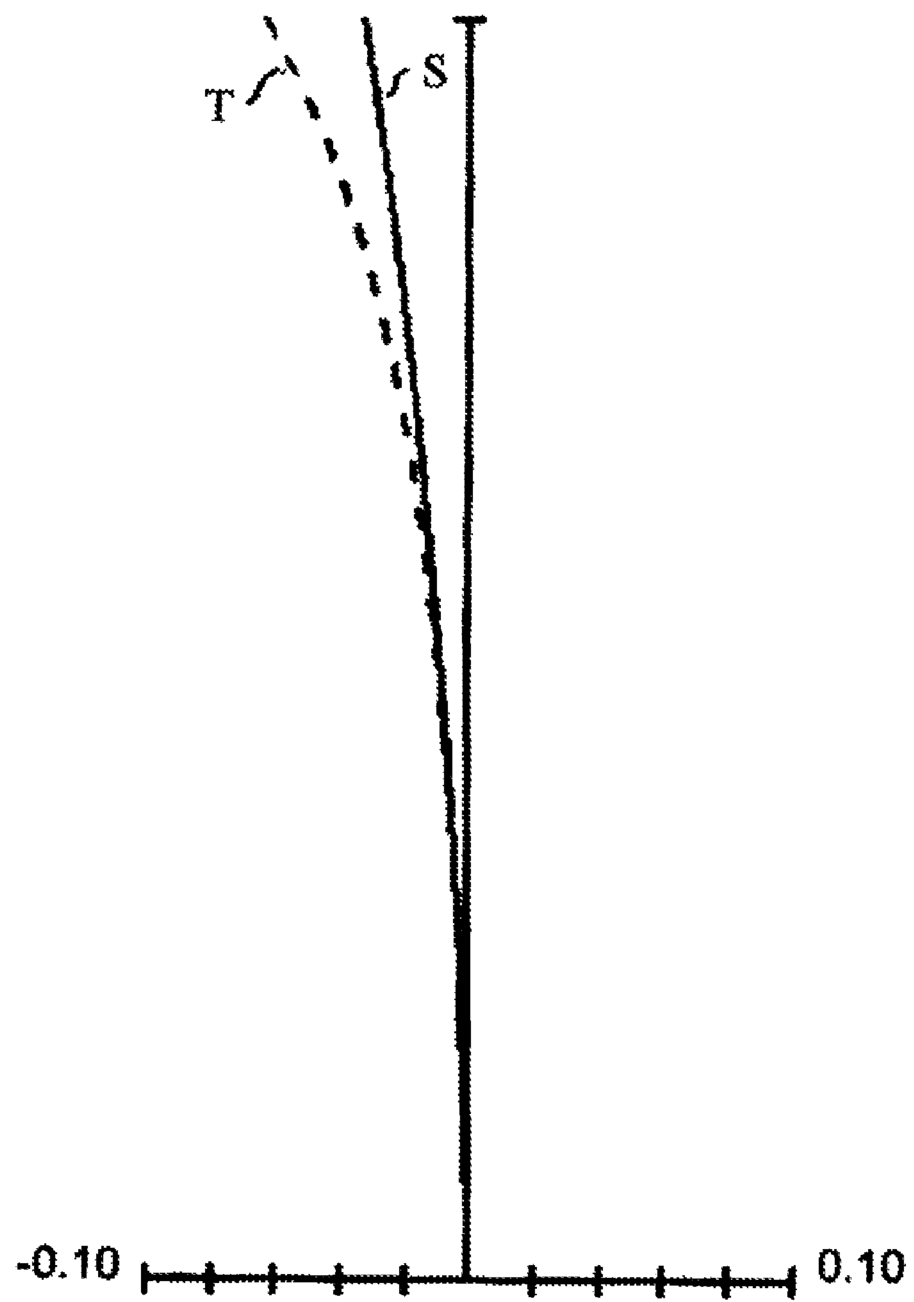
FIG. 12 shows the curvature of field when a spherical surface is viewed using the capsule endoscope according to Embodiment 5.

FIG. 12 shows the curvature of field of the objective optical system 92' shown in FIG. 11 when the maximum angle of view is set at 90° and a hemispherical surface region having a radius of curvature R equal to 4.5 mm is regarded as the object. In FIG. 12, the horizontal axis indicates the distance from the paraxial image plane, and the vertical axis indicates the height of the image. It is understood that the surface of 'best focus' is situated midway between the sagittal image to surface S and the tangential image surface T. As is apparent from FIG. 12, the surface of 'best focus' is obviously a concave surface that is orientated toward the object side.

In Embodiment 5, focusing enables a setting where $a_0$=0.5 mm; the distance from a near point to a far point on the axis is approximately 11 mm, and a total viewing angle range of approximately 60° or greater on the surface of the transparent cover is situated within the depth of field.

Table 2 below lists the performance and construction data of the objective optical system 92' of Embodiment 5. In the top portion of the table are listed the focal length f, the position of the front focal point $f_F$, the position of the back foal point $f_B$, the image height IH, and the field of view θ. In the middle portion of the table, in the left column, are listed the radii of curvature of each surface, starting with the radius of curvature of the surface nearest the object side (r1) and ending with the image surface. In the second column are listed the on-axis surface spacing from the surface having the radius of curvature listed in the left column on the same line to the next surface, in order from the object side. In the third column are listed the index of refraction of the optical material of each lens element. Where no index of refraction is listed in the third column, the optical medium is air, having an index of refraction of unity. In the fourth column are listed the Abbe number of the optical material having the index of refraction as listed in the third column for the same line. The index of refraction ni aid Abbe number υi that are listed are relative to the d-line. In the bottom portion of the table am listed the values of interest in calculating Conditions (1), (2) and (5).

TABLE 2 f = 0.936, $f_F$ = −0.016, $f_B$ = −0.012
IH = 0.666, θ = 86.3°, $X_B$ = −7.5

| | | | |
|---|---|---|---|
| r1 = ∞ | d1 = 0.24 | n1 = 1.51825 | ν1 = 63.9 |
| r2 = 1.2730 | d2 = 0.09 | | |
| r3 = ∞ (diaphragm) | d3 = 0.03 | | |
| r4 = ∞ | d4 = 0.95 | n4 = 1.88815 | ν4 = 40.5 |
| r5 = −1.0730 | d5 = 0.08 | | |
| r6 = ∞ | d6 = 0.49 | n6 = 1.88815 | ν6 = 40.5 |
| r7 = −2.1070 | d7 = 1.06 | | |
| r8 = ∞ (image plane) | d8 = 0 | | |

Values of interest in calculating Conditions (1), (2) and (5):

| | |
|---|---|
| Condition (1) | Because ΔS equals −0.09 and ΔT equals −0.10, \|ΔI\| equals −0.095; $2f^2\{1-\cos(\theta max/2)\}/D\cdot\cos(\theta max/2)$ equals 0.08. Therefore, the two terms on the left-hand side of the Condition (1) are such that 0.08-0.095 equals −0.015. |
| Condition (2) | IHmax/f equals 0.71 |
| Condition (5) | Because P = 0.39, and D equals 9, the right-hand side of Condition (5), i.e., p · D, equals 3.51, and the left-hand side of Condition (5), i.e., $2f^2\{1-\cos(\theta max/2)\}/IHmax^2\cdot\cos(\theta max/2)$ equals 1.64. |

TABLE 2-continued f = 0.936, $f_F$ = −0.016, $f_B$ = −0.012
IH = 0.666, θ = 86.3°, $X_B$ = −7.5

The invention being thus described, it will be obvious that the same may be varied in many ways. For example, among the above-mentioned built-in components, any components which do not relate to the essence of the present invention can freely be substituted. Such variations are not to be regarded as a departure from the spirit and scope of the invention. Rather, the scope of the invention shall be defined as set forth in the following claims and their legal equivalents. All such modifications as would be obvious to the skilled in the art are intended to be included within the scope of the following claims.

What is claimed is:

1. A capsule endoscope comprising:

a capsule having a central axis;

an illumination light source;

an objective optical system that forms images of a region illuminated by the illumination light emitted from the illumination light source, the objective optical system having a depth of field, a field of view, and an image surface that has curvature of field such that, the higher the image height becomes, the greater the image surface tilts toward the object side;

an image pickup device that receives the images formed by the objective optical system; and a transparent cover having a central axis and located in front of the objective optical system; wherein the objective optical system is arranged on the central axis of the transparent cover and the capsule;

at the periphery of the field of view, the transparent cover has a radius of curvature substantially equal to one-half the outside diameter of the capsule; and the near point of the depth of field along the optical axis of the objective optical system is positioned farther from the transparent cover than is the distance along the optical axis of the objective optical system from the transparent cover to a hypothetical hemispherical surface having a radius equal to one-half the outside diameter of the capsule and that is positioned to enclose the capsule in front of the objective optical system.

2. The capsule endoscope according to claim 1, wherein the image pickup device is arranged so that an image receiving surface thereof is positioned at a point that is conjugate, with regard to the objective optical system, to the intersection point of the hypothetical hemispherical surface and the optical axis of the objective optical system.

* * * * *